United States Patent [19]

Toniolo

[11] Patent Number: 4,926,453
[45] Date of Patent: May 15, 1990

[54] MAMMOGRAPHY APPARATUS

[75] Inventor: Bruno Toniolo, Sasso Marconi, Italy

[73] Assignee: I.M.S. Internazionale Medico Scientifica s.r.l., Pontecchio Marconi, Italy

[21] Appl. No.: 407,529

[22] Filed: Sep. 15, 1989

[30] Foreign Application Priority Data

Mar. 17, 1989 [IT] Italy .................................. 3386 A/89

[51] Int. Cl.⁵ .............................................. A61B 6/04
[52] U.S. Cl. ...................................... 378/37; 378/197
[58] Field of Search ................... 378/37, 197, 196, 195

[56] References Cited

U.S. PATENT DOCUMENTS 2,818,510  12/1957  Verse .................................... 378/197

Primary Examiner—Craig E. Church
Attorney, Agent, or Firm—Hoffmann & Baron

[57] ABSTRACT

Conventional mammography apparatus comprises a stand with a vertically adjustable slide, and X-ray equipment mounted to a horizontal shaft carried by the slide and capable of rotating about its own longitudinal axis; in apparatus as disclosed, the appliance is mounted to a frame, carried by the shaft and rotatable about an axis other than the axis of the shaft. The frame comprises an inner annular or segmental member that rolls internally of a similar outer member mounted to the horizontal shaft, in such a way as to adjust for position by rotation about an axis normal to the shaft.

5 Claims, 3 Drawing Sheets

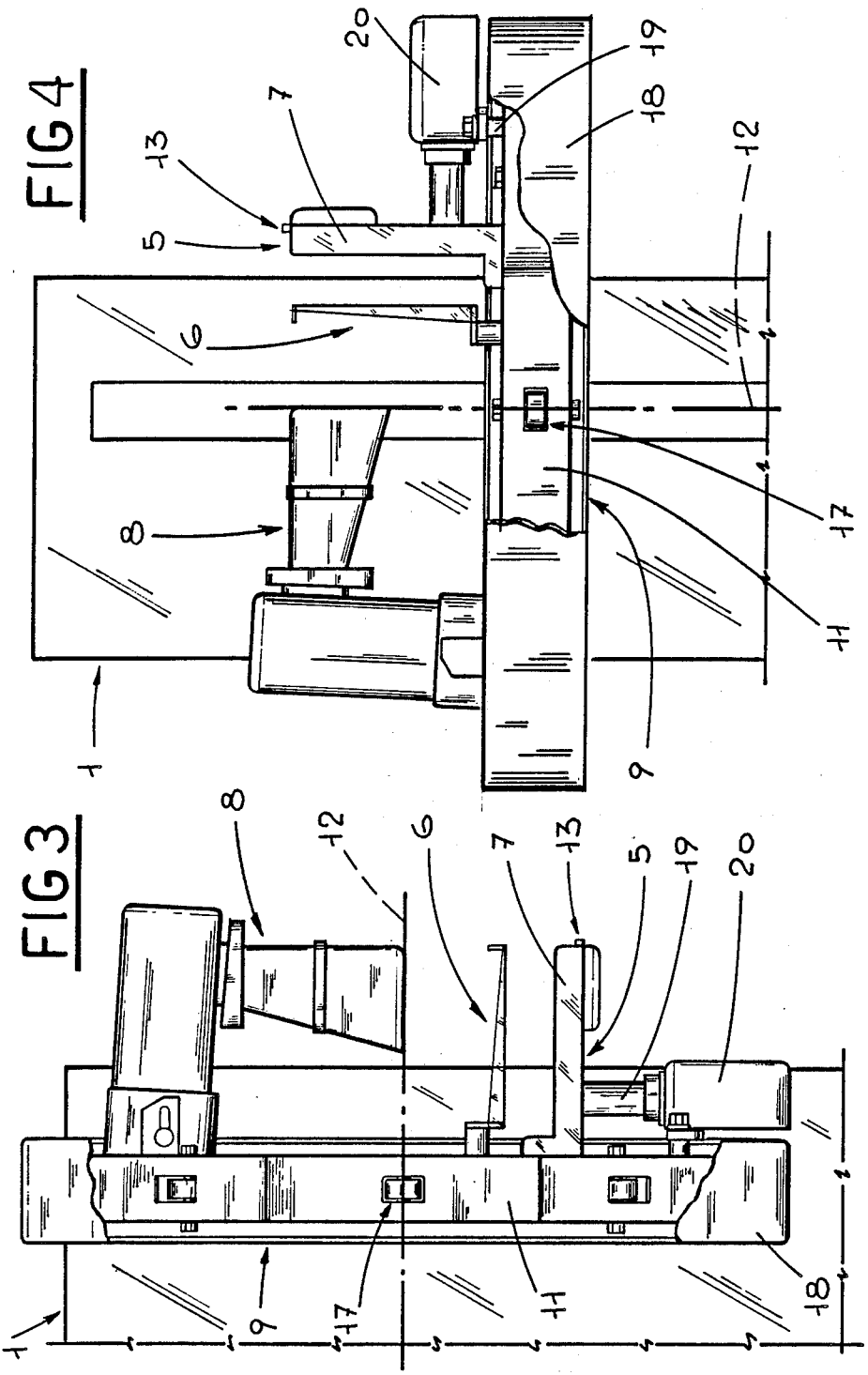

MAMMOGRAPHY APPARATUS

BACKGROUND OF THE INVENTION

The present invention relates to apparatus for effecting mammography.

The art field of X-ray equipment embraces a variety of types of apparatus, differing primarily on the basis of the particular application.

One such particular application is that of breast X-ray examination, the radiographic appliance for which comprises a container accommodating an X-ray film destined to receive the image, and an X-ray source directed at the film; in addition, use is made of means located between the film and the source, against which to rest, and if necessary, to compress the breasts under examination.

The X-ray appliance is mounted to a horizontally disposed shaft, the shaft in turn being carried on a height-adjustable slide capable of traversing up and down an upright stand.

The fit between the horizontal shaft and the slide is such that the shaft can be rotated about its own longitudinal axis, together with the appliance.

This rotation facility is of fundamental importance in enabling X-ray images to be taken from different angles, and more exactly, avoiding the possibility that one image only be generated precisely in the shadow of the suspected foreign body, or lump, i.e. in a direction along which the lump might remain transparent to or hidden from the X-rays.

Clearly, a successful mammography requires that the breasts be offered to and accurately positioned on the rest; this is a procedure carried out by the radiographer, whose task it is also to ensure that no shift in position occurs during the examination. With existing apparatus, however, such requirements bring difficulty for the operator and/or discomfort to the patient, as the radiographer is obliged to adjust the position of the patient's breasts while standing alongside or behind her.

Stationed alongside the patient, the radiographer's movement is inevitably restricted by the presence of the stand on the one side, and on the other, of a patient who obviously must remain motionless. The second position mentioned, i.e. behind the patient, is impractical for several reasons, not least of which being the impossibility of seeing how the patient's breasts are in fact disposed on the rest.

Accordingly, the object of the invention is to embody X-ray apparatus for mammography such as can give the radiographer greater freedom of movement, at least for the purpose of verifying the correct position of a patient's breasts when offered to the apparatus: in short, allowing the radiographer to operate with the patient positioned facing opposite throughout the examination, and thus ensure that her breasts are correctly disposed on the rest.

A further object of the invention is to allow the patient freedom of posture, i.e. the possibility of remaining upright, standing or sitting, supine, or again, inclined forward with the breasts hanging in order to induce any suspected lump lower during the examination, and thus enhance the X-ray.

SUMMARY OF THE INVENTION

The stated objects are achieved with mammography apparatus according to the present invention.

Apparatus of the general type in question comprises an X-ray appliance rigidly associated with a shaft that is horizontally disposed, rotatable about its own longitudinal axis and carried by a slide that can be adjusted for height by traversing vertically on an upright stand.

In apparatus as disclosed, the X-ray appliance associates with the horizontal shaft by way of a rolling frame capable of giving further positional adjustment by rotation about an axis other than that of the shaft.

One of the advantages gained with X-ray apparatus according to the invention is the complete freedom of movement afforded to the radiographer, who is able to remain facing the patient while adjusting the position of her breasts on the rest.

Another advantage of the invention is that of the more simple movements accomplished by the apparatus itself, inasmuch as the rest is positioned in close proximity to an axis of rotation and therefore can be kept substantially at a constant height.

BRIEF DESCRIPTION OF THE DRAWINGS

The invention will now be described in detail, by way of example, with the aid of the accompanying drawings, in which:

FIGS. 3 and 4 are side elevations of the apparatus disclosed, shown in two different configurations.

DESCRIPTION OF THE PREFERRED EMBODIMENTS

Figure 1:
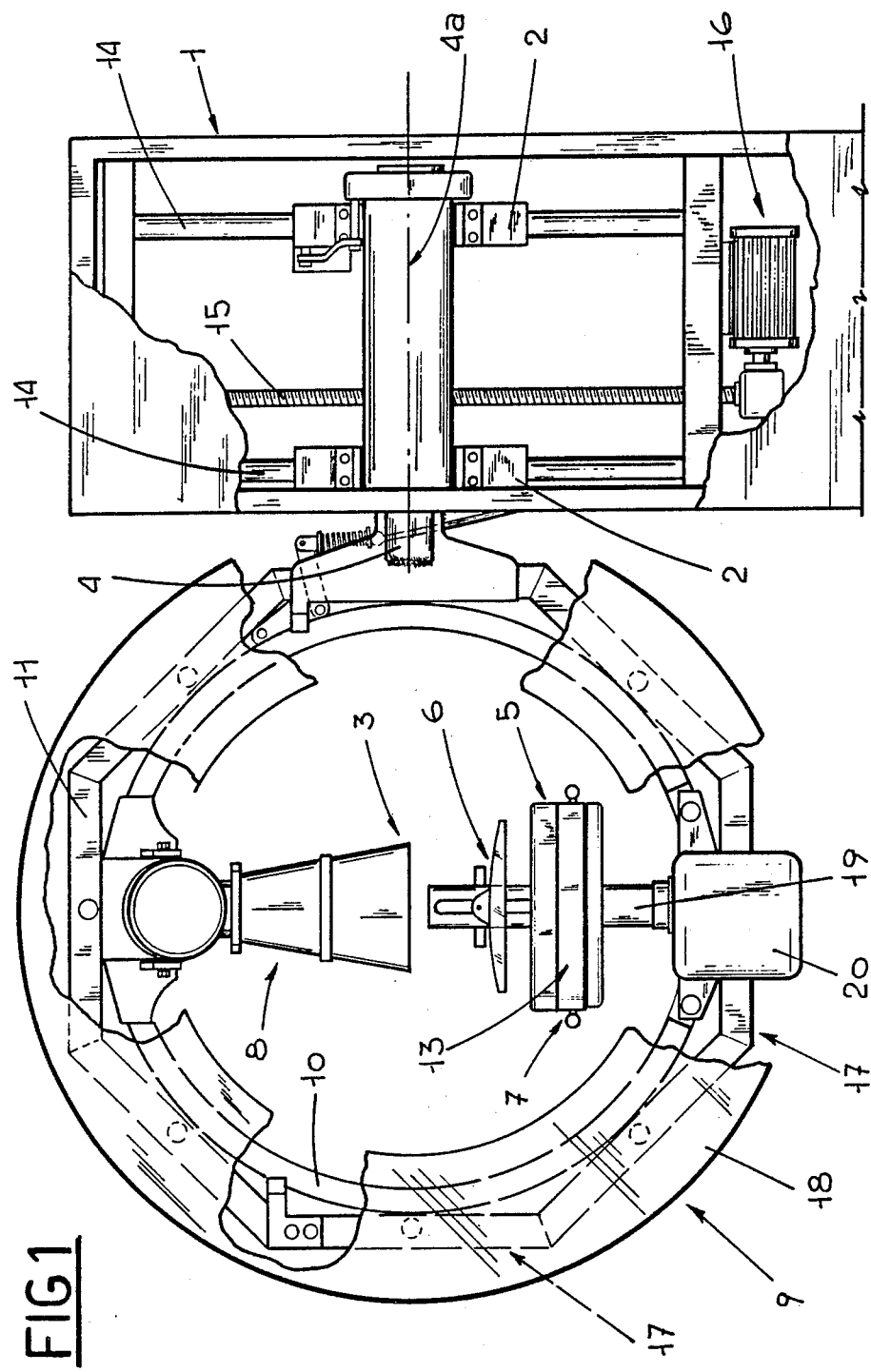
FIGS. 1 and 2 are vertical elevations of apparatus according to the present invention, viewed from the standpoint of the patient and showing the X-ray appliance in two distinct angular positions.
Figure 2:
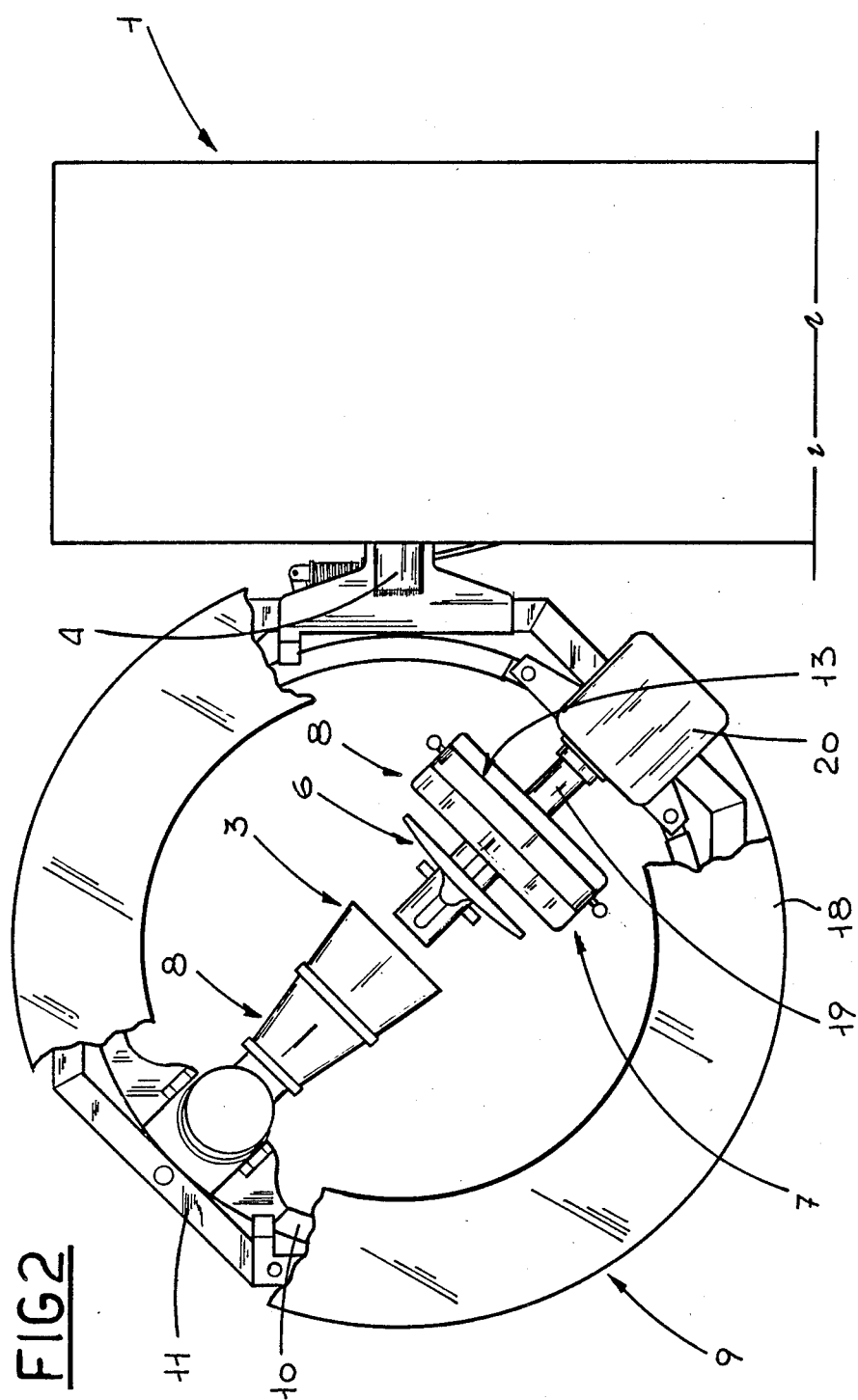

With reference first to FIGS. 1 and 2, apparatus according to the invention comprises a vertical pillar, or stand 1, and an X-ray appliance proper, which is denoted 3 in its entirety.

2 denotes a height-adjustable slide carried by the stand 1; the adjustment might be obtained by means of an arrangement as illustrated in FIGS. 1 and 2, comprising two vertical rods 14 and a lead screw 15 permanently associated with and located inside the stand, which pass freely through and engage with a thread in the body of the slide 2, respectively.

The lead screw 15 is rotated in one direction and the other by a geared motor 16, also located inside the stand 1.

4 denotes a horizontal shaft carried by the slide 2 and rotatable about its own longitudinal axis 4a, whether manually or by means of a respective geared motor not illustrated in the drawings.

The X-ray appliance 3, mounted to the horizontal shaft 4, comprises means 5 and 6 for the support and compression of the breasts of a patient under examination, a container 7 housing the X-ray film, and an X-ray source 8 by which an image is produced on the film.

In apparatus according to the present invention, the X-ray appliance 3 is carried in a frame 9 that can be adjusted for position by rotation about an axis 12 other than the longitudinal axis 4a of the horizontal shaft 4.

In the particular embodiment illustrated by way of example, the frame 9 consists in a first, circular annular element 10 supported by a second annular element 11, which might be circular, or polygonal as shown in FIGS. 1 and 2, where it can be observed that the one element 10 is disposed internally of and substantially in the same plane as the other element 11.

The outer element 11 is associated rigidly with the shaft 4, disposed substantially in the same plane, and affords a plurality of bearings 17 projecting from its inward facing surface, by which the inner annular element 10 is supported; in the embodiment illustrated, the bearings 17 are rotatable about respective axes disposed normal to the shaft 4, and accordingly, the inner element 10 can be rolled about an axis 12 normal to the shaft axis 4a.

Rotation of the inner element 10 can be produced either manually, or utilizing power in the form of a geared motor (not illustrated) housed internally of a casing 18 by which the entire frame 9 will be enclosed; in operation, the inner element 10 and the outer element 11 will be afforded a degree of angular movement between two essentially horizontal limit positions of the order of 180° approximately, rolling and rotating about the axis denoted 12 and the horizontal shaft axis 4a, respectively.

The X-ray appliance 3 is mounted diametrically to the inner element 10, and more exactly, with the source 8 on one side of center, and the container 7 and the support and compression means 5 and 6 on the other.

The support and compression means 5 and 6 consist essentially in a rest 5, incorporated into one side of the film container 7, and a movable compression plate 6 that can be drawn closer to and distanced from the rest 5 through a mutually parallel path, by conventional means that are not illustrated. The container 7 and the compression plate 6 are mounted to a sleeve 19 rigidly associated with the inner element 10 and adjustable for position along the axis of the sleeve by either manually-operated or power-driven means, accommodated in a relative housing 20, which will be of a type able to produce micrometric movement.

It is discernible from FIGS. 3 and 4 that the X-ray appliance 3 occupies one face of the frame 9, and that the edge 13 of the rest 5 offered to the ribs of the patient lies parallel to the plane by which the frame 9 is accommodated.

The apparatus thus described will comprise numerous other components of conventional embodiment, such as electrical connections to the various geared motors and the X-ray source 8, casings that protect and complete the appearance of the equipment, and mechanisms by which the inner element 10 and the entire frame 9 are locked into selected positions; such items do not constitute subject matter of the appended claims however, and accordingly, further description is unnecessary.

With apparatus embodied thus, the patient can be positioned standing, leaning forward, sitting or even reclining in front of the frame 9 with the radiographer stationed on the far side of the frame facing toward her; accordingly, the radiographer has no difficulty in verifying the position of the patient's breasts when offered to the rest 5, and of extracting best possible results from the X-ray examination.

A further advantage of apparatus embodied in the manner described is that a screen can be located directly in front of the patient, separating both the radiographer and the monitoring and control equipment from the apparatus, to the end of gaining still more accurate control over the examination. In the event that the breasts of a patient are to be X-rayed in a hanging posture, the shaft 4 will be rotated to the point where the frame 9 lies either horizontal or angled between vertical and horizontal, with the appliance 3 directed upwards, whereupon the slide 2 can be lowered on the stand 1 and the frame 9 brought down to a level such as will enable a couch, bearing the patient, to be positioned above.

The foregoing description is strictly indicative; in an alternative embodiment of the apparatus, the elements 10 and 11 might be segmental rather than fully circular, though in this instance the arc of movement available to the inner element 10 must necessarily be less than 180°; again, the outer element 11 might be angled relative to the shaft 4, within the same plane, or set in a plane other than that occupied by the shaft axis 4a.

What is claimed

1. Mammography apparatus, comprising:
   an upright stand;
   a slide supported by and adjustable for height in relation to the stand;
   horizontal shaft associated with the slide and rotatable about its own longitudinal axis;
   an X-ray appliance comprising means by which to support and compress the breasts of a patient under examination, means in which to contain X-ray film, and a source of X-rays located opposite the support and compression means;
   a frame, to which the X-ray appliance is mounted, permanently associated with the horizontal shaft and adjustable for position by rotation about a given axis that is disposed skew and/or offset in relation to the longitudinal axis of the shaft.

2. Mammography apparatus, comprising:
   an upright stand;
   a slide supported by and adjustable for height in relation to the stand;
   a horizontal shaft associated with the slide and rotatable about its own longitudinal axis;
   an X-ray appliance comprising means by which to support and compress the breasts of a patient under examination, means in which to contain X-ray film, and a source of X-rays located opposite the support and compression means;
   a frame, to which the X-ray appliance is mounted, permanently associated with the horizontal shaft and adjustable for position by rotation about an axis disposed normal to the longitudinal axis of the shaft.

3. Apparatus as in claim 2, comprising a frame embodied as a first element of unbroken or broken periphery occupying a plane lying parallel to the horizontal shaft and carried by a second element of unbroken or broken periphery rigidly attached to the horizontal shaft, wherein the two elements of unbroken or broken periphery are coaxial, and rotatable one in relation to the other about an axis disposed normal to that of the horizontal shaft.

4. Apparatus as in claim 2, comprising a frame embodied as an annular element occupying a plane lying parallel to the horizontal shaft and carried by a second element of unbroken periphery rigidly attached to the horizontal shaft, wherein the annular element is disposed internally of and coaxial with the element of unbroken periphery, and rotatable in relation thereto about an axis disposed normal to that of the horizontal shaft.

5. Apparatus as in claim 2, wherein the support and compression means are embodied with an edge, offered to the ribs of a patient, that is disposed substantially normal to the axis of rotation of the frame.

* * * * *